US00PP19254P3

(12) United States Plant Patent
Austin

(10) Patent No.: US PP19,254 P3
(45) Date of Patent: Sep. 23, 2008

(54) ***ROSA HYBRIDA* SHRUB NAMED 'AUSPASTOR'**

(50) Latin Name: *Rosa hybrida*
Varietal Denomination: AUSpastor

(75) Inventor: David C. H. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 11/904,127

(22) Filed: Sep. 26, 2007

(65) Prior Publication Data

US 2008/0134371 P1 Jun. 5, 2008

(51) Int. Cl.
*A01H 5/00* (2006.01)

(52) U.S. Cl. ..... Plt./103

(58) Field of Classification Search ..... Plt./103
See application file for complete search history.

*Primary Examiner*—Annette H Para
*Assistant Examiner*—S. B. McCormick-Ewoldt
(74) *Attorney, Agent, or Firm*—Kauth, Pomeroy, Peck & Bailey LLP

(57) ABSTRACT

A variety of rose plant of the shrub class, named 'AUSpastor' suitable for cut flower production is disclosed. The 'AUSpastor' rose is a plant suitable for year round production under standard greenhouse conditions having buttermilk-colored blooms that fade to almost white with an Old Rose fragrance and long vase life, which are produced on strong upright stems.

1 Drawing Sheet

CROSS-REFERENCE TO RELATED APPLICATIONS

The current application claims priority to European Breeder's Right Certificate Application No. 2006/2288, filed Nov. 13, 2006 and Kenyan Breeder's Right Certificate Application No. ROS 07 834, filed Feb. 16, 2007, the disclosures of which are incorporated herein by reference.

Classification: The present invention relates to a new *Rosa hybrida* shrub.

Variety denomination: The new plant has the varietal denomination 'AUSpastor'.

ORIGIN OF INVENTION

This invention relates to a new and distinct variety of shrub rose plant named 'AUSpastor', which was originated by crossing two unnamed, unpatented varieties of *Rosa hybrida.*

BACKGROUND OF THE INVENTION

The primary objective of this breeding was to produce a plant suitable for year round production under standard greenhouse conditions having buttermilk-colored blooms that fade almost to white, with an Old Rose fragrance and long vase life, which are produced on strong upright stems.

SUMMARY OF THE INVENTION

Among the features which distinguish the new variety from other presently available and commercial rose cultivars known to the inventor is the following combination of characteristics: butter-milk colored blooms fading almost to white, an Old Rose fragrance and a long vase life. The plant also has a strong upright stem, which makes it suitable for year round cut flower production under standard greenhouse conditions.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSpastor' may be asexually propagated by budding and grafting. The budding and grafting successfully occurred on the plant/rootstock *Rosa* cv. 'Natal Briar'.

COMPARISON WITH PARENTS

The new rose maybe distinguished from its seed parent, by the following combination of characteristics: whereas the parent has lilac cupped blooms, 'AUSpastor' bears buttermilk colored, rosette shaped blooms.

The new variety may be distinguished from its pollen parent, by the following combination of characteristics: whereas the pollen parent bears yellow blooms with pointed petals, 'AUSpastor' bears flowers of a buttermilk color. In addition, the new variety bears blooms that are quartered, whereas the pollen parent bears bears yellow colored, rosette shaped blooms.

The new variety is classified as a *hybrida* rose with a strong upright growing habit and has obovate shaped petals with a notched margin.

COMPARISON WITH THE CLOSEST COMMERCIALLY AVAILABLE CULTIVAR

The closest commercially available cultivar to the new variety is the 'AUSneil' [U.S. Pat. No. 17,317]. The new rose may be distinguished from the 'AUSneil' variety by the following combination of characteristics: the 'AUSneil' has fewer petals, stamens and creamy-white blooms compared to 'AUSpastor', which has a greater number of petals, creamy-white blooms with a hint of blush and no stamens.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society [2001] except where common terms of color definition are employed.

DESCRIPTION OF THE NEW VARIETY

The following description is of 2 year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Continuous. The number of blooms per plant during the growing season is profuse, but there are too many to count.

*Bud.*—Size: About 2.7 cm long and 1.9 cm in diameter when the petals start to unfurl. Form: The bud form is pointed ovoid. Color: When sepals first divide, the bud color is Yellow Group 3C. When half blown, the upper sides of the petals are White Group 155B with Yellow Group 3D at base and the lower sides of the petals are White Group 155C with Yellow Group 3D at the base. Calyx: Shape: [from above] irregularly rounded. Length: 3.5 cm. Diameter: 3.5 cm. Sepals: Arrangement: Regular. Color: Upper Surface: Green Group 143A with Yellow-Green Group 144D at the base. Lower Surface: Yellow-Green Group 144A with Yellow-Green Group 146A along margin and appendages. Length: 2.9 cm. Width: 0.9–1 cm. Shape: Subulate. Margin: Canescent. Surface texture: Upper Surface: Pubescent. Lower Surface: Smooth. Number: There are three normally appendaged sepals. There are 2 unappendaged sepals with hairy edges. Receptacles: Color: Yellow-Green Group 144A. Shape: other campanulate. Size: small, about 0.7 cm×1.1 cm. Surface: Smooth. Peduncle: Length: medium, averaging about 9 cm. Surface: Smooth [few small prickles]. Color: Yellow-Green Group 144A. Strength: Strong.

*Blooms.*—Size: Large, average open diameter is about 8.3 cm. Borne: Singly in clusters of 2–4 [buds are nipped out to leave a single bloom] blooms having corymb shaped inflorescence. Stems: Strength: Strong, average length is about 30–50 cm. Diameter: 5 mm. Form: When first open, bloom is cupped. Permanence of bloom: Retains its form to the end flattens and all petal curl.

*Petalage.*—Number of petals under normal conditions: 160–170. Color: The upper sides of the petals are White Group 155C. The reverse sides of the petals are White Group 155C. The base of the petals is Yellow Group 3D. Variegations: N/A. Discoloration: The general tonality at the end of the first day is White Group 155C with Yellow Group 3D at base and at the end of the third day is White Group 155A with 155C at margin and Yellow Group 3D at base. Fragrance: Strong. Character of fragrance: Old Rose.

*Petals.*—Texture: Smooth, satiny. Size: Width: 3.8 cm. Length: 3.9 cm. Surface: Smooth. Shape: Obovate, the very outer petals are obdeltoid. Margin: Notched. Apex Shape: Cuspidate [outer petals are rounded]. Base Shape: Cuneate. Form: Incurved; tips are recurved and undulating. Arrangement: Imbricated [central petals are scrolled]. Petaloids: Not present. Persistence: Petals drop off cleanly before drying. Lastingness: On the plant: long, about 12 days. As a cut flower: fair, about 10 days.

*Reproductive parts.*—Stamens: Not present. Pistils: Number: 70. Length: 10–11 mm. Styles: Color: Yellow Group 1C. Length: 9 mm. Stigmas: Color: Yellow-Green Group 151D. Length: 1–2 mm. Hips: None Observed.

Plant characteristics:

*Plant form.*—Shrub [grown solely for cut flower production].

*Plant growth.*—Vigorous and upright.

*Age to maturity.*—One year.

*Mature plant.*—Height: 1.2 m. Width: 0.8 m.

*Rootstock.*—*Rosa* 'Natal Briar' for the observed plants.

*Foliage.*—Number: Leaflets on normal mid-stem leaves is: 5–7 [including terminal leaflet]. Size: Medium, about 13.5 cm long×9.6 cm wide. Quantity: Normal. Number of leaves per flowering stem is: 10. Color: New foliage: Upper side: Green Group 137A overlaid Greyed-Purple Group 183A, which is more intense around margin. Lower side: Yellow-Green Group 144A overlaid with Greyed-Purple Group 184B. Old foliage: Upper side: Green Group 139A or Green Group 137A. Lower side: Green Group 137C or Green Group 138B.

*Leaflets.*—Size: About 5.3 cm long×3.7 cm wide. Shape: Ovate. Base Shape: Rounded. Apex Shape: Cuspidate. Texture: Smooth. Edge: Serrated. Serrations: Single large. Petiole: Color: Yellow-Green Group 144A under side and Yellow-Green Group 146A upper side. Length: 3.8 cm. Width: 1 mm. Surface Texture: Smooth, a few glands. Petiole Rachis: Color: Yellow-Green Group 144A. Underside: Smooth [a few glands]. Stipules: Length: 2.5–3 cm glandular. Color: Green Group 143B. Auricle: Shape: Elongated awl. Length: 6–8 mm. Width: 1 mm tapering to point. Color: Green Group 143B. Vein Color: Yellow-Green Group 144B. Venation Pattern: Reticulate.

*Wood.*—New Wood: Color: Yellow-Green Group 144A. Bark: Smooth. Old Wood: Color: Yellow-Green Group. 144A overlaid with Greyed-Red Group 178A. Bark: Smooth.

*Branching habit.*—Lateral Branch Dimensions: Length: 30 cm. Diameter: 5 mm.

*Stems.*—Mature Stem: Length: 30–50 cm. Diameter: 5 mm. Internode Distance: Length: 5–6 cm. The above measurements are all variable, depending on growing conditions in a season. Stem Pubescence Present: No.

*Prickles.*—Quantity: On main canes from base: ordinary. Number per stem length: 3 per 5 cm. On laterals from main canes: ordinary. Number per stem length: 3 per 5 cm. Form: Concave curved inward.

Length: 9 mm. Color when young: Greyed-Red Group 178C and Yellow-Green Group 144C at base. Color when mature: Greyed-Yellow Group 160D.

*Small prickles.*—Quantity: Main stalk: None. Number per stem length: None. Laterals: None.

*Disease resistance.*—Mildew: Resistant. Blackspot: Resistant. Rust: Resistant.

*Pest resistance.*—Not tested.

*Winter hardiness.*—Not tested.

*Growing conditions.*—Special. Greenhouse rose for cut flower production; disbud where necessary to leave one bloom per stem.

What is claimed is:

1. A new and distinct variety of rose plant of the shrub class suitable for cut flower production in greenhouse conditions, substantially as herein shown and described.

* * * * *

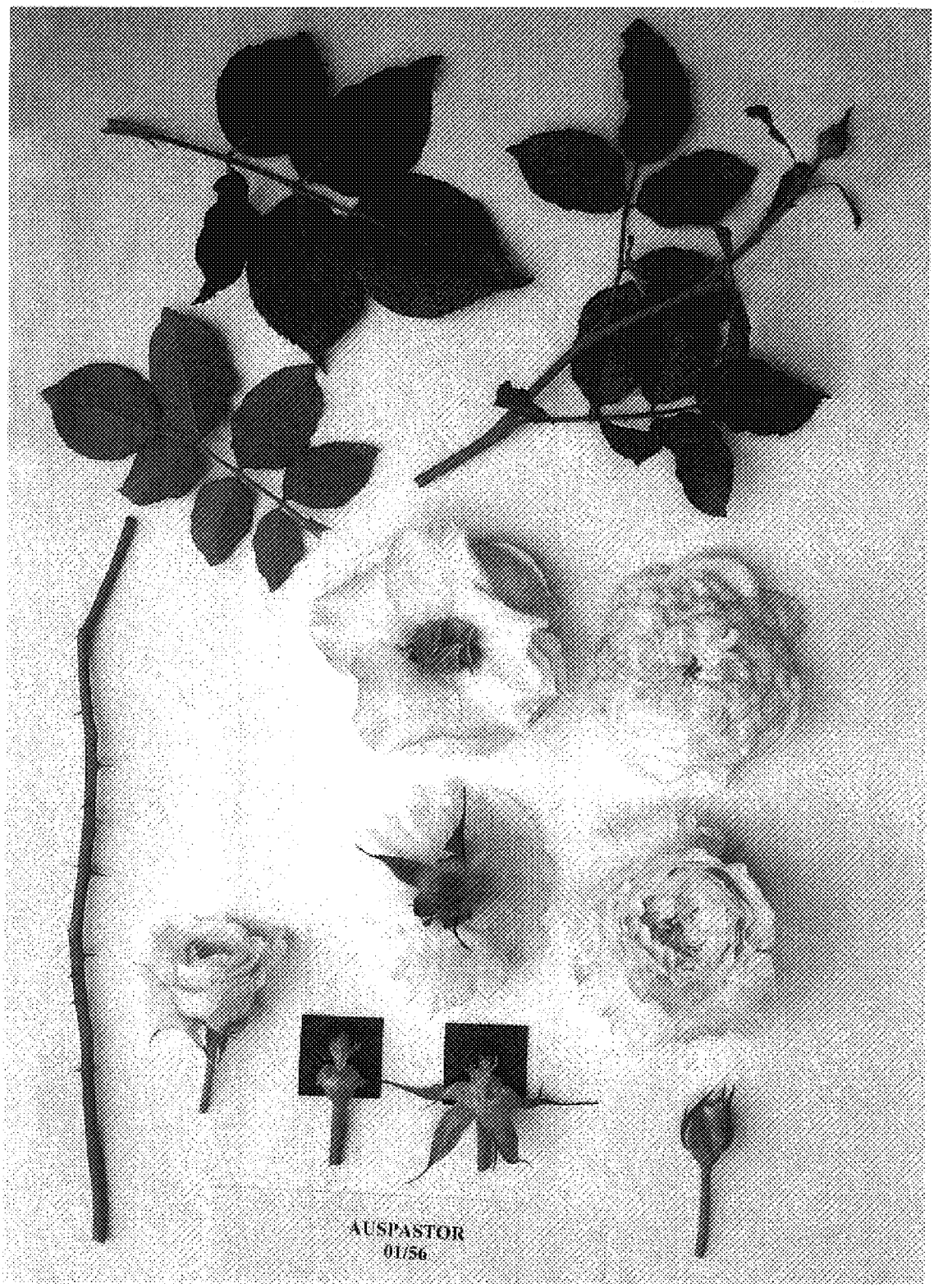
AUSPASTOR
01/56